(12) United States Patent
Ohkubo et al.

(10) Patent No.: US 8,456,638 B2
(45) Date of Patent: Jun. 4, 2013

(54) OPTICAL MEASUREMENT APPARATUS, OPTICAL MEASUREMENT SYSTEM, AND FIBER COUPLER

(75) Inventors: Kazuaki Ohkubo, Kusatsu (JP); Kunikazu Taguchi, Hirakata (JP)

(73) Assignee: Otsuka Electronics Co., Ltd., Hirakata-Shi (JP)

( * ) Notice: Subject to any disclaimer, the term of this patent is extended or adjusted under 35 U.S.C. 154(b) by 175 days.

(21) Appl. No.: 13/034,711

(22) Filed: Feb. 25, 2011

(65) Prior Publication Data

US 2011/0235036 A1 Sep. 29, 2011

(30) Foreign Application Priority Data

Mar. 25, 2010 (JP) .................. 2010-069964

(51) Int. Cl.
*G01N 21/55* (2006.01)
(52) U.S. Cl.
CPC ..................................... *G01N 21/55* (2013.01)
USPC ....................................................... 356/445
(58) Field of Classification Search
CPC .................................................... G01N 21/55
USPC ......................................... 356/445–448, 236
See application file for complete search history.

(56) References Cited

U.S. PATENT DOCUMENTS

| 7,283,222 B1* | 10/2007 | Ohkubo et al. ............... 356/213 |
| 7,521,667 B2* | 4/2009 | Rains et al. ................... 250/228 |
| 2005/0156103 A1 | 7/2005 | May et al. |

FOREIGN PATENT DOCUMENTS

| JP | 60-202411 | 10/1985 |
| JP | 63-285441 | 11/1988 |
| JP | 1-124723 | 5/1989 |
| JP | 7-212537 | 8/1995 |
| JP | 2003-527619 | 9/2003 |
| JP | 2005-055571 | 3/2005 |

* cited by examiner

*Primary Examiner* — Michael P Stafira
(74) *Attorney, Agent, or Firm* — Ditthavong Mori & Steiner, P.C.

(57) ABSTRACT

An optical measurement apparatus includes a spectroscopic measurement device, a first optical fiber for propagating light to be measured, a hemispherical portion having a light diffuse reflection layer on an inner wall of the hemispherical portion, and a plane portion disposed to close an opening of the hemispherical portion and having a mirror reflection layer located to face the inner wall of the hemispherical portion. The plane portion includes a first window for directing the light emitted thorough the first optical fiber into an integrating space. The integrating space is formed by the hemispherical portion and the plane portion. The optical measurement apparatus further includes a second optical fiber for propagating the light in the integrating space to the spectroscopic measurement device through a second window of the plane portion.

19 Claims, 10 Drawing Sheets

US 8,456,638 B2

OPTICAL MEASUREMENT APPARATUS, OPTICAL MEASUREMENT SYSTEM, AND FIBER COUPLER

BACKGROUND OF THE INVENTION

1. Field of the Invention

The present invention relates to an optical measurement apparatus and an optical measurement system that enable reduction of measurement errors due to variation in the distribution of light emitted from an optical fiber, as well as a fiber coupler directed thereto.

2. Description of the Background Art

A technique of measuring optical characteristics of an object to be measured, by means of a spectroscopic optical system, has conventionally been known. More specifically, where the object to be measured is a light emitting body (light source), spectrum, light source color, brightness, illuminance, and quantum efficiency, for example, of the light emitted from the object are measured. Further, where the object to be measured is a non-light-emitting body, reflectance or transmittance, and/or absorbance, for example, is measured, based on the reflected light or transmitted light obtained from irradiation of the object with light. Further, in some cases, from the optical characteristics thus measured, a physical amount such as the film thickness of the object to be measured is calculated.

Methods of reducing measurement errors in such spectroscopic measurement have been proposed. For example, Japanese Patent Laying-Open No. 01-124723 discloses a configuration that enables reduction of measurement errors due to wavelength-dependent polarization characteristics.

In contrast to the use of spectroscopic measurement as described above, a configuration in which an integrating sphere is used as a light source apparatus to homogenize or mix the light from a light source has been known (for example, Japanese Patent Laying-Open Nos. 60-202411, 63-285441, and 07-212537, Japanese National Patent Publication No. 2003-527619, Japanese Patent Laying-Open No. 2005-055571, and U.S. Patent Application Publication US2005/0156103A1).

Spectroscopic measurement could involve, in addition to measurement errors due to polarization characteristics as described above, measurement errors due to variation of the light distribution. Typically, while light to be measured propagates in an optical fiber, variation of the transmittance could cause variation in the distribution of the light emitted from the optical fiber. Such variation of the light distribution results in uneven brightness on a light-receiving surface of a spectroscopic measurement device.

In the case where a plurality of light rays to be measured are propagated through a plurality of optical fibers respectively and measured with a common spectroscopic measurement device, these optical fibers have to be optically coupled to one optical fiber. In such a case, if variation of the light distribution occurs as described above, the amount of optical coupling varies, which results in a problem that the amount of light for example directed to the spectroscopic measurement device also varies.

SUMMARY OF THE INVENTION

The present invention has been made to solve these problems, and an object of the invention is to provide an optical measurement apparatus and an optical measurement system that enable reduction of measurement errors due to variation in the distribution of light emitted from an optical fiber, as well as a fiber coupler directed thereto.

An optical measurement apparatus according to an aspect of the present invention includes a spectroscopic measurement device, a first optical fiber for propagating light to be measured, a hemispherical portion having a light diffuse reflection layer on an inner wall of the hemispherical portion, and a plane portion disposed to close an opening of the hemispherical portion and having a mirror reflection layer located to face the inner wall of the hemispherical portion. The plane portion includes a first window for directing the light emitted through the first optical fiber into an integrating space. The integrating space is formed by the hemispherical portion and the plane portion. The optical measurement apparatus further includes a second optical fiber for propagating the light in the integrating space to the spectroscopic measurement device through a second window in the plane portion.

An optical measurement apparatus according to another aspect of the present invention includes a spectroscopic measurement device, a first optical fiber for propagating light to be measured, a quarter-spherical portion having a light diffuse reflection layer on an inner wall of the quarter-spherical portion, and a first plane portion and a second plane portion disposed to close an opening of the quarter-spherical portion and each having a mirror reflection layer located to face the inner wall of the quarter-spherical portion. One of the first plane portion and the second plane portion includes a first window for directing the light emitted through the first optical fiber into an integrating space. The integrating space is formed by the quarter-spherical portion, the first plane portion, and the second plane portion. The optical measurement apparatus further includes a second optical fiber for propagating the light in the integrating space to the spectroscopic measurement device through a second window in the one of the first and second plane portions to which the first optical fiber is connected.

Preferably, the first optical fiber includes a plurality of optical fiber elements each propagating the light to be measured.

Preferably, at the plane portion, the first window and the second window are arranged apart from each other by a predetermined distance.

Preferably, the first optical fiber and the second optical fiber are integrated to pass through the plane portion.

An optical measurement system according to still another aspect of the present invention includes a light source, a spectroscopic measurement device, a light splitter for dividing light from the light source into a plurality of light source components, a first optical fiber for propagating a plurality of light components depending on a characteristic of an object to be measured that are obtained by applying the plurality of light source components from the light splitter to the object to be measured, a hemispherical portion having a light diffuse reflection layer on an inner wall of the hemispherical portion, and a plane portion disposed to close an opening of the hemispherical portion and having a mirror reflection layer located to face the inner wall of the hemispherical portion. The plane portion includes a first window for directing light emitted through the first optical fiber into an integrating space. The integrating space is formed by the hemispherical portion and the plane portion. The optical measurement system further includes a second optical fiber for propagating the light in the integrating space to the spectroscopic measurement device through a second window in the plane portion.

According to a further aspect of the present invention, a fiber coupler connected to an input side of a spectroscopic measurement device is provided. The fiber coupler includes a hemispherical portion having a light diffuse reflection layer on an inner wall of the hemispherical portion, and a plane portion disposed to close an opening of the hemispherical portion and having a mirror reflection layer located to face the inner wall of the hemispherical portion. The plane portion includes a first window connected to a first optical fiber for propagating light to be measured and directing light emitted through the first optical fiber into an integrating space. The integrating space is formed by the hemispherical portion and the plane portion, and a second window connected to a second optical fiber for propagating the light in the integrating space to the spectroscopic measurement device.

The present invention enables reduction of measurement errors due to variation in the distribution of light emitted from an optical fiber.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
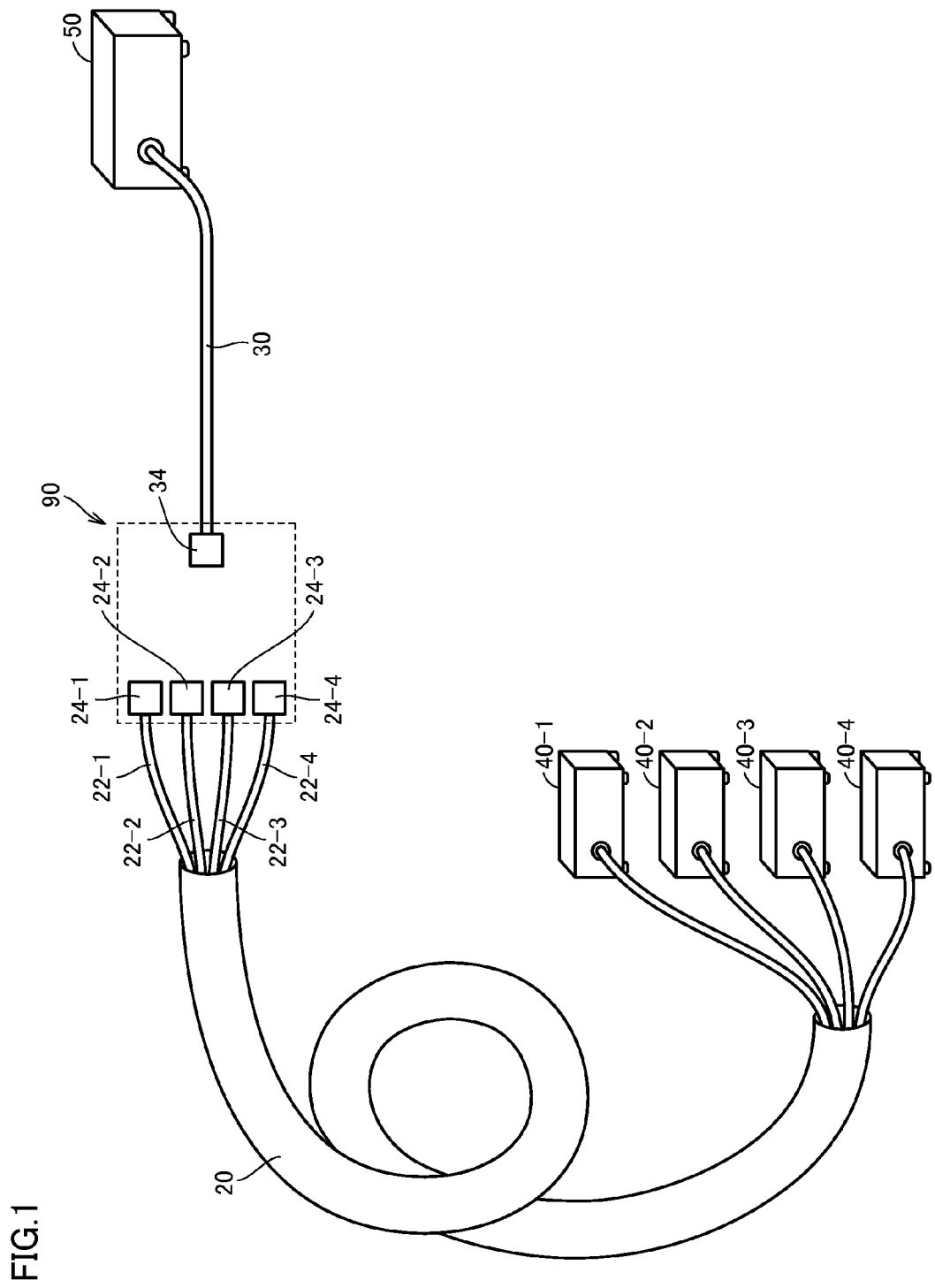
FIG. 1 schematically shows an example of an optical measurement apparatus using a fiber coupler that is relevant to the present invention.

An embodiment of the present invention will be described in detail with reference to the drawings. In the drawings, the same or corresponding components are denoted by the same reference characters, and a description thereof will not be repeated.

<A. Overview>

An optical measurement apparatus according to the present embodiment has a fiber coupler formed of a hemispherical integrator or a quarter-spherical integrator that is provided on the input side of a spectroscopic measurement device to thereby reduce measurement errors due to variation in the distribution of light emitted from an optical fiber.

<B. Relevant Art>

First, a configuration relevant to the present invention will be described.

b1. Opposite Arrangement Type

Referring to FIG. 1, an optical measurement apparatus using a fiber coupler that is relevant to the present invention will be described.

FIG. 1 shows an example of an optical system that uses a spectroscopic measurement device in a shared manner to measure a plurality of light rays to be measured. The optical system shown in FIG. 1 spectroscopically measures the light rays to be measured that are supplied from light source apparatuses 40-1, 40-2, 40-3, and 40-4 (hereinafter also referred to as "light source apparatus 40" collectively), and includes a fiber coupler 90, an incidence side fiber 20, an emission side fiber 30, and a spectroscopic measurement device 50.

Each light source apparatus 40 emits light generated from an internal lamp or the like. The light generated at each light source apparatus 40 is directed though incidence side fiber 20 to fiber coupler 90. Namely, incidence side fiber 20 propagates the light to be measured to fiber coupler 90.

Fiber coupler 90 couples the light rays to be measured that have been generated respectively by light source apparatuses 40, and then directs the resultant light to spectroscopic measurement device 50 through emission side fiber 30. Namely, fiber coupler 90 is an optical device for optically coupling a plurality of optical fibers (fiber elements) and one optical fiber (fiber element).

Spectroscopic measurement device 50 detects the spectrum of the light to be measured that has been introduced through emission side fiber 30. Typically, spectroscopic measurement device 50 is configured to include a diffraction grating and a line sensor or the like associated with the directions of diffraction of the diffraction grating, and outputs the intensity of the input light for each wavelength. Further, spectroscopic measurement device 50 can perform, based on the result of detection of the spectrum, evaluation of the essential performance of the light source such as chromaticity, illuminance, brightness, and color rendering index, measurement of the optical performance of the object to be measured such as surface characteristics, reflection characteristics, and transmission characteristics, and measurement of physical amounts of the object to be measured such as film thickness.

In fiber coupler 90, a plurality of fiber elements 22-1, 22-2, 22-3, 22-4 (hereinafter also referred to as "fiber element 22" collectively) each that constitute incidence side fiber 20, and one fiber element of emission side fiber 30 are substantially aligned with a single optical axis to thereby implement optical coupling. Specifically, respective fiber ends 24-1, 24-2, 24-3, 24-4 (hereinafter also referred to as "fiber end 24" collectively) of fiber elements 22-1, 22-2, 22-3, 22-4, and a fiber end 34 of emission side fiber 30 are arranged opposite to and away from each other by a predetermined distance.

Where a plurality of fiber elements 22 (fiber ends 24) constituting incidence side fiber 20 and the fiber element of emission side fiber 30 are arranged directly opposite to each other, however, it is difficult to allow respective states of light rays emitted respectively from fiber elements 22 of incidence side fiber 20 and illuminating the fiber element of emission side fiber 30 to be identical to each other. Consequently, the optical paths extending respectively through fiber elements 22 to spectroscopic measurement device 50 cannot have the same transmissibility, resulting in variation of measured values, depending on the type of the fiber element used for measurement.

In other words, the configuration in which the fiber elements are arranged opposite to each other causes variation of the amount of light transmitted to emission side fiber 30, because of variation of the distribution of light emitted from incidence side fiber 20.

It is thus required to design the configuration so that it is not influenced by such variations. In generally used fiber coupler 90, a transmissive diffusion plate is disposed and, at its opposing ends, a plurality of fiber elements constituting incidence side fiber 20 and one fiber element of emission side fiber 30 are arranged opposite to each other.

Figure 2A:
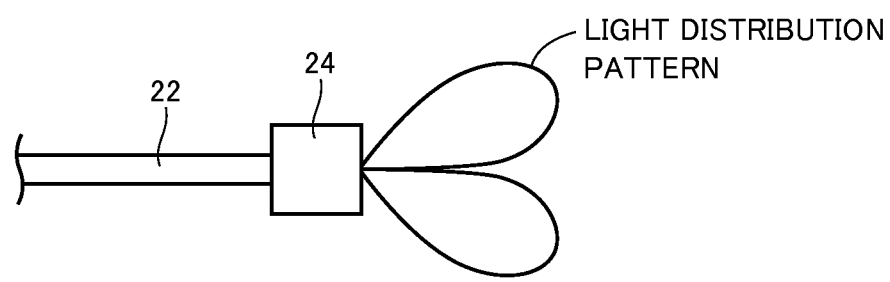
FIGS. 2A and 2B are diagrams for illustrating variation of light distribution in the fiber coupler shown in FIG. 1.
Figure 2B:
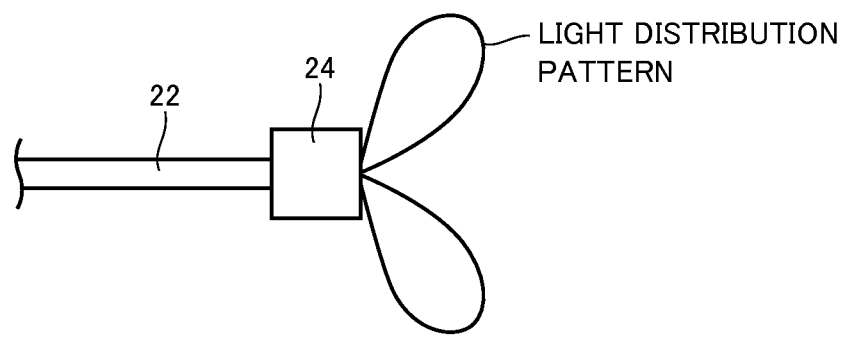

By way of example, FIGS. 2A and 2B each show an example of variation in the distribution pattern of the light emitted from fiber end 24 of fiber element 22. As shown in FIGS. 2A and 2B, the variation in the light distribution pattern of incidence side fiber 20 causes a change in the ratio of light that reaches emission side fiber 30.

Figure 3:
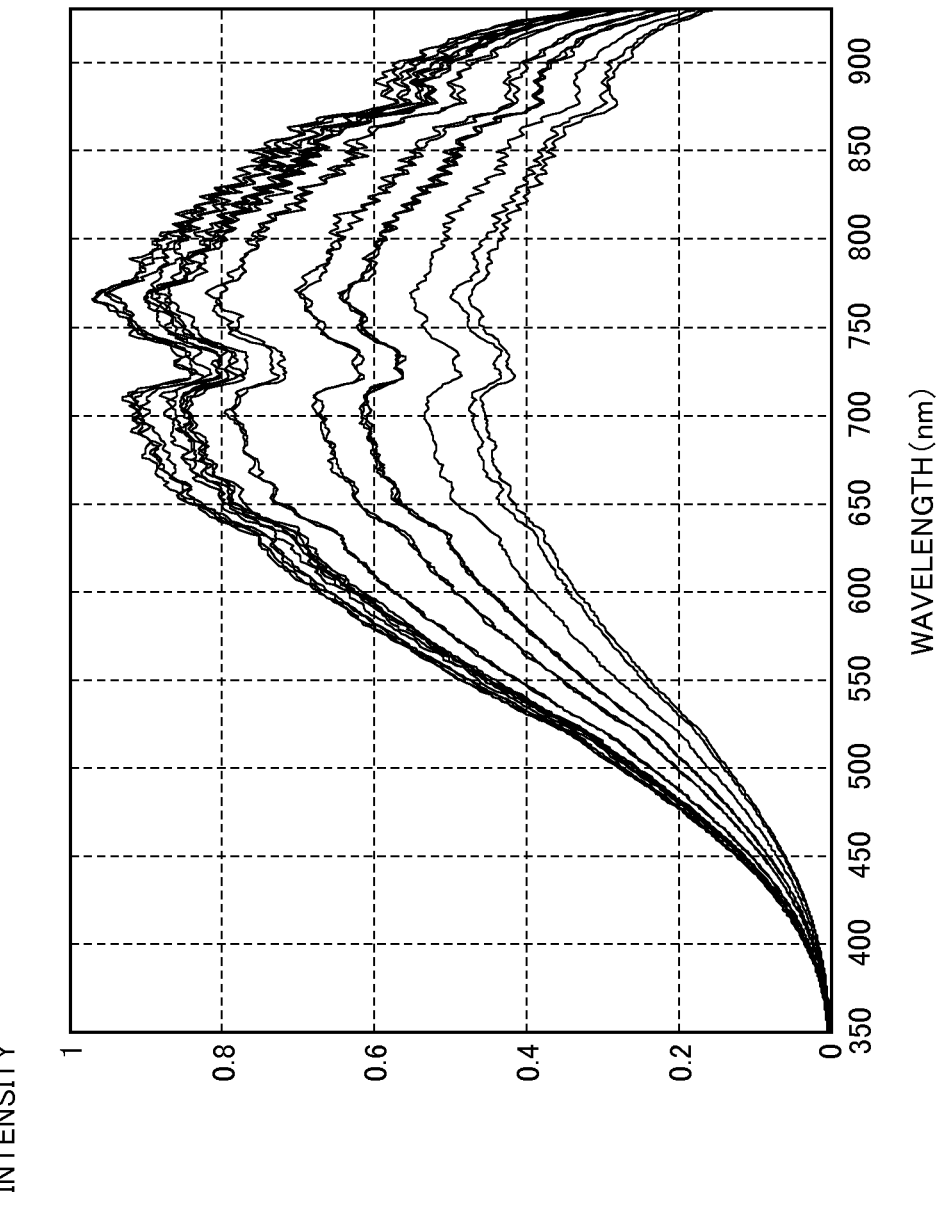
FIG. 3 shows an experimental result regarding variation of light distribution in the fiber coupler shown in FIG. 1.

FIG. 3 shows an experimental result regarding variation of the light distribution in the fiber coupler shown in FIG. 1. This experiment used a fiber coupler where incidence side fiber 20 and emission side fiber 30 are arranged opposite to and away from each other by 15 mm. In this configuration, incidence side fiber 20 was intentionally bent while the light from light source apparatus 40 was measured multiple times by means of spectroscopic measurement device 50. The experimental result (result of spectroscopic measurement) is shown in FIG. 3. As light source apparatus 40, a halogen lamp was used and, no transmissive diffusion plate is placed between incidence side fiber 20 and emission side fiber 30. Further, an optical bench was used to position incidence side fiber 20 and emission side fiber 30.

From the experimental result shown in FIG. 3, it is seen that bending of incidence side fiber 20 causes the intensity of the measured spectrum to considerably vary. The reason for this appears to be that bending of incidence side fiber 20 causes variation in the distribution of light emitted from incidence side fiber 20. The variation of the light distribution may occur regardless of the type of incidence side fiber 20 (multimode fiber and single mode fiber), namely may occur to both fiber types.

In order to lessen the influence of such variation in the light distribution to thereby make uniform the transmissibility of the optical paths extending through respective fiber elements 22 to spectroscopic measurement device 50, it is necessary to have a sufficiently long distance between incidence side fiber 20 and emission side fiber 30 or have a relatively high diffusivity of the transmissive diffusion plate.

Any of these methods employed, however, leaves a problem that the light transmission loss increases and the measurement sensitivity deteriorates.

b2. Integrating Sphere Type

Instead of the above-described fiber coupler, an integrating sphere may be used to optically couple incidence side fiber 20 and emission side fiber 30. This integrating sphere is formed of a spherical member having a light diffuse reflection layer on its inner surface, and incidence side fiber 20 and emission side fiber 30 extend through a predetermined position of the spherical member to be connected to an integrating space in the integrating sphere.

In the case where this integrating sphere is used, a luminous flux emitted from incidence side fiber 20 illuminates the whole inner surface of the integrating sphere, and the resultant light associated with the illuminance at the inner wall surface is transmitted to emission side fiber 30. Thus, illuminance E measured through emission side fiber 30 may be represented by expression (1) as shown below where the luminous flux emitted from incidence side fiber 20 into the integrating space is denoted by $\phi$:

$$\text{Illuminance } E=(\phi/4\pi r^2)\{\rho/(1-\rho)\} \quad (1)$$

where r represents the radius of the integrating sphere and $\rho$ represents the diffuse reflectance of the inner surface of the integrating sphere.

As seen from this expression (1), a smaller radius r of the integrating sphere provides a higher intensity of the light measured through emission side fiber 30. Namely, the transmission efficiency from incidence side fiber 20 to emission side fiber 30 is higher.

However, if the light emitted from incidence side fiber 20 directly enters emission side fiber 30, it is difficult to keep the same illumination conditions among respective fiber elements 22 and, if the distribution of light emitted from incidence side fiber 20 varies, the efficiency of transmission from incidence side fiber 20 to emission side fiber 30 varies.

In order to lessen the influences as described above, it is required to provide a baffle (light blocking plate) in the integrating sphere so that the light emitted from incidence side fiber 20 does not directly enter emission side fiber 30. In the case, however, where the integrating sphere is designed to have a smaller radius for the purpose of increasing the efficiency of transmission from incidence side fiber 20 to emission side fiber 30, the ratio of the space occupied by the baffle to the integrating space is relatively higher, resulting in an apparent reduction in the amount of light due to absorption of light by the baffle itself. A resultant problem is thus a disadvantageous increase of the transmission loss of the light, leading to deterioration in measurement sensitivity.

<C. Basic Configuration>

An optical measurement apparatus according to the present embodiment aims to overcome the problems of the fiber coupler and the integrating sphere as described above.

Figure 4:
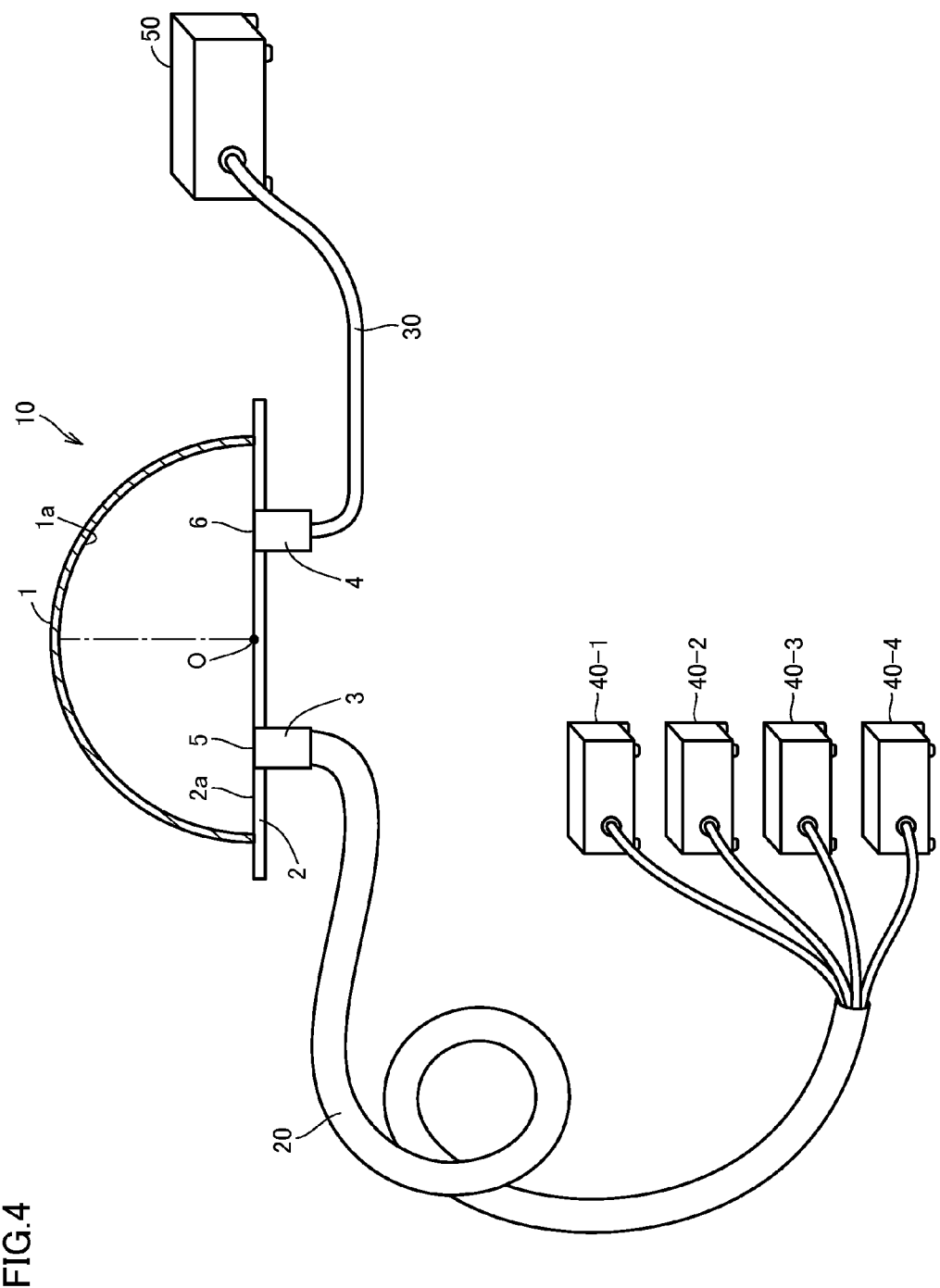
FIG. 4 schematically shows an example of an optical measurement apparatus according to an embodiment of the present invention.

The optical measurement apparatus according to the embodiment of the present invention shown in FIG. 4 differs from the optical measurement apparatus shown in FIG. 1 in that a fiber coupler 10 using a hemispherical integrator is employed instead of the opposite-arrangement-type fiber coupler 90.

Fiber coupler 10 is formed of a hemispherical portion 1 having a diffuse reflection layer 1a on its inner wall, and a disk-shaped plane portion 2 disposed to close an opening of the hemispherical portion. Plane portion 2 has a mirror reflection layer 2a located to face the inner wall (inner surface) of hemispherical portion 1. Plane portion 2 is disposed to include a substantial center of curvature O of hemispherical portion 1. Diffuse reflection layer 1a is formed exemplarily by applying or spraying a light diffusing material such as sintered polytetrafluoroethylene (PTFE) or barium sulfate.

Since mirror reflection layer 2a of plane portion 2 is arranged opposite to the inner wall of hemispherical portion 1, a virtual image of hemispherical portion 1 is created. As described above, plane portion 2 is disposed to include the center of curvature O of hemispherical portion 1, and therefore, the virtual image created by plane portion 2 is in the shape of a hemisphere having a constant radius of curvature. The space (real image) defined by the inner surface of hemispherical portion 1 and the virtual image created by plane portion 2 can be combined to obtain an illuminance distribution that is substantially identical to that obtained when a full-sphere type integrator is used.

As seen from the above, in fiber coupler 10, the space that is a combination of the space (real image) defined by the inner surface of hemispherical portion 1 and the virtual image created by plane portion 2 is provided as a substantial integrating space.

Plane portion 2 includes an incidence window 5 for directing the light emitted through incidence side fiber 20 into the integrating space formed by hemispherical portion 1 and plane portion 2. To incidence window 5, a connection coupler 3 formed at the leading end of incidence side fiber 20 is attached.

The light directed through incidence side fiber 20 into the integrating space is repeatedly diffuse-reflected within the integrating sphere made up of hemispherical portion 1 and the virtual image of hemispherical portion 1 that is created by plane portion 2, and consequently the illuminance at the inner wall of hemispherical portion 1 is made uniform.

Plane portion 2 further includes an emission window 6 formed for attaching emission side fiber 30 thereto. To this emission window 6, a connection coupler 4 formed at the leading end of emission side fiber 30 is attached. Thus, the light in the integrating space is directed through emission side fiber 30 to spectroscopic measurement device 50.

The positional relation between incidence window 5 and emission window 6 of plane portion 2 is not limited to a specific one. In the example shown in FIG. 4, incidence window 5 and emission window 6 are disposed apart from each other by a predetermined distance with respect to the substantial center of curvature O of hemispherical portion 1.

In the case where fiber coupler 10 is used, the number of fiber elements 22 that constitute incidence side fiber 20 and each for propagating the light to be measured is not particularly limited. Specifically, since one or a plurality of light rays to be measured that is directed into the integrating space formed by hemispherical portion 1 and plane portion 2 is repeatedly reflected in the integrating space, the light (illuminance E) directed through emission side fiber 30 to spectroscopic measurement device 50 has a value representing the sum of the light rays to be measured that have been directed into the integrating space.

As described above, incidence window 5 and emission window 6 are both formed at the plane portion. Namely, these windows are located on the common plane and therefore the light from incidence window 5 does not directly enter emission window 6. More specifically, since incidence window 5 and emission window 6 are not at the positions that allow the windows to be irradiated each other, a baffle (light blocking plate) between the windows is unnecessary, in contrast to the case where a full-sphere-type integrator is used.

Therefore, the problem of reduction in the amount of light due to absorption of light by the baffle itself does not arise. Further, because the baffle provided inside is unnecessary, the integrating space can further be downsized. Namely, since the radius of curvature of hemispherical portion 1 can further be reduced, the intensity of the light measured through emission side fiber 30 can be increased as seen from expression (1). In other words, fiber coupler 10 with a high efficiency of transmission from incidence side fiber 20 to emission side fiber 30 can be achieved.

Other features are similar to those of the optical measurement apparatus shown in FIG. 1, and the detailed description thereof will not be repeated.

Figure 5:
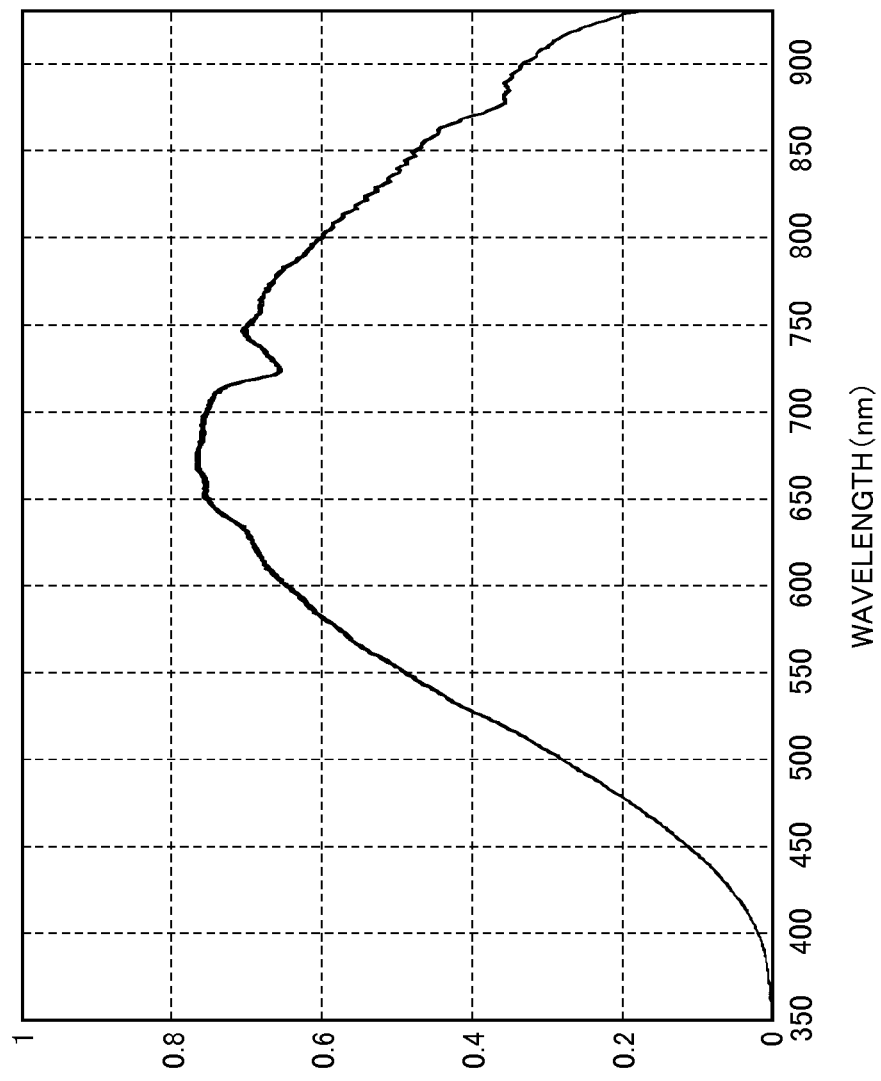
FIG. 5 shows an experimental result regarding variation of light distribution in a fiber coupler shown in FIG. 4.

An experimental result regarding variation of the light distribution in the fiber coupler shown in FIG. 4 is illustrated in FIG. 5. FIG. 5 shows the result of measurement where the light from light source apparatus 40 is measured multiple times by spectroscopic measurement device 50 while incidence side fiber 20 of the optical measurement apparatus shown in FIG. 4 is intentionally bent (result of spectroscopic measurement). It is noted that as light source apparatus 40 a halogen lamp is used similarly to the experimental result shown in FIG. 3 as described above.

It is seen from the experimental result shown in FIG. 5 that even if incidence side fiber 20 is bent, there is no substantial influence on the spectrum measured. More specifically, the ratio of variation of the spectrum that occurred due to bending of incidence side fiber 20 is not more than 0.1%. As seen from the above, the influence of variation in the distribution of light emitted from incidence side fiber 20 is substantially negligible.

<D. Modification> d1. Fiber-Integrated Type

Regarding the optical measurement apparatus shown in FIG. 4, its configuration has been illustrated in which incidence window 5 and emission window 6 for attaching incidence side fiber 20 and emission side fiber 30 respectively are formed at plane portion 2. In an alternative configuration, incidence side fiber 20 and emission side fiber 30 may be integrated to pass through plane portion 2.

Figure 6:
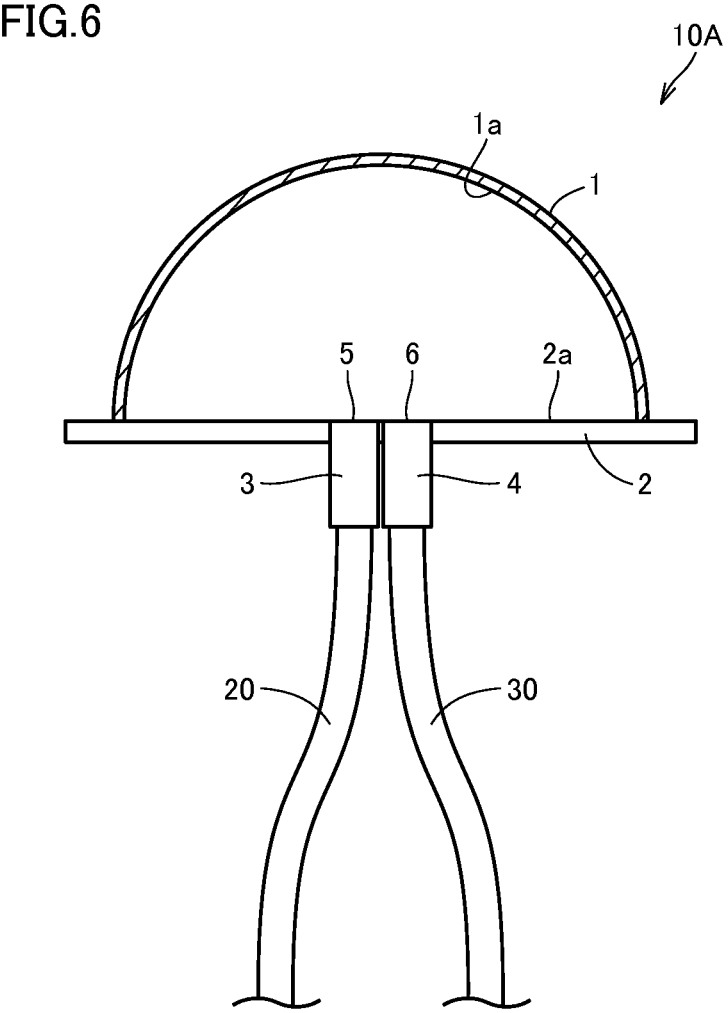
FIG. 6 schematically shows a fiber coupler according to a first modification of the embodiment of the present invention.

FIG. 6 schematically shows a fiber coupler 10A according to a first modification of the embodiment of the present invention. In fiber coupler 10A shown in FIG. 6, incidence window 5 and emission window 6 are formed adjacent to each other. It is noted that incidence window 5 and emission window 6 may integrally be formed. In this case, one common window functions as incidence window 5 and emission window 6.

Incidence side fiber 20 and emission side fiber 30 in the integrated state pass through plane portion 2. While FIG. 6 schematically shows a configuration where a connection coupler 3 formed at the leading end of incidence side fiber 20 is attached to incidence window 5 and a connection coupler 4 formed at the leading end of emission side fiber 30 is attached to emission window 6, the connection couplers themselves may be formed to serve as a common connection coupler.

It is noted that incidence side fiber 20 constituted of a plurality of fiber elements may be used. In this case, a plurality of fiber elements constituting incidence side fiber 20 and one fiber element that forms emission side fiber 30 may also be integrated.

The optical measurement apparatus according to the first modification of the present embodiment is similar to that of FIG. 4 except that fiber coupler 10A is used, and therefore, the detailed description thereof will not be repeated.

In this way, incidence side fiber 20 and emission side fiber 30 are integrated, and accordingly a process of connecting fibers to fiber coupler 10A can be facilitated.

d2. Quarter-Spherical Integrator

Regarding the optical measurement apparatus shown in FIG. 4, a configuration where fiber coupler 10 for which a hemispherical integrator is used has been illustrated. Instead, a quarter-spherical integrator may also be used.

Figure 7:
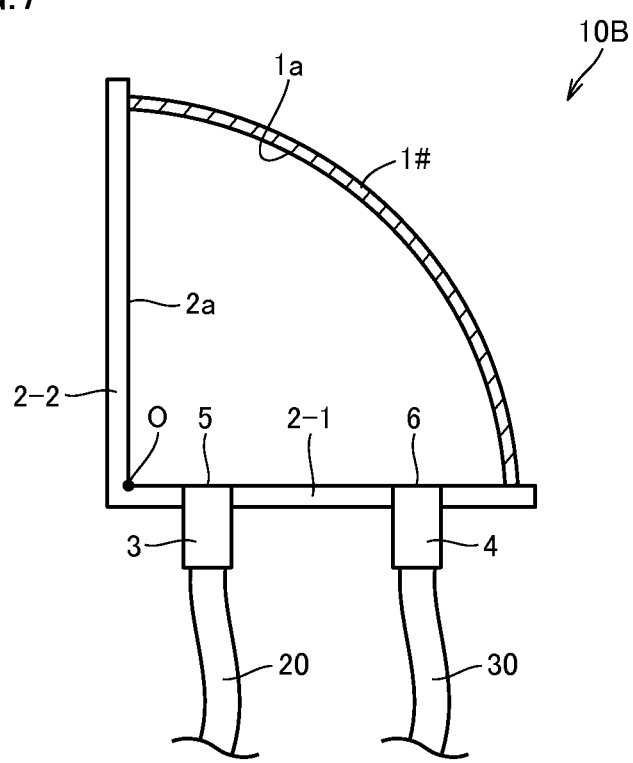
FIG. 7 schematically shows a fiber coupler according to a second modification of the embodiment of the present invention.

FIG. 7 schematically shows a fiber coupler 10B according to a second modification of the embodiment of the present invention. Fiber coupler 10B shown in FIG. 7 includes a quarter-spherical portion 1# having a diffuse reflection layer 1a on its inner wall, and semicircular plane portions 2-1, 2-2 disposed to close the opening of the quarter-spherical portion and having a mirror reflection layer 2a located opposite the inner wall (inner surface) of quarter-spherical portion 1#. The interface between plane portion 2-1 and plane portion 2-2 is disposed to include the substantial center of curvature O of quarter-spherical portion 1#.

Mirror reflection layer 2a of plane portion 2-1 is disposed opposite the inner wall of quarter-spherical portion 1#, so that a virtual image of quarter-spherical portion 1# is created (on the lower side on the drawing). Likewise, mirror reflection layer 2a of plane portion 2-2 is disposed opposite the inner wall of quarter-spherical portion 1#, so that a virtual image of quarter-spherical portion 1# is created (on the left side on the drawing). As described above, the interface between plane portion 2-1 and plane portion 2-2 is disposed to include the substantial center of curvature O of quarter-spherical portion 1#. Therefore, the space (real image) defined by the inner surface of quarter-spherical portion 1# and respective virtual images created by plane portion 2-1 and plane portion 2-2 can be combined to obtain the illuminance distribution substantially identical to that obtained when a full-sphere type integrator is used.

As seen from the above, in fiber coupler 10B, the space formed by combining the space (real image) defined by the inner surface of quarter-spherical portion 1# and respective virtual images created by plane portions 2-1 and 2-2 is a substantial integrating space. At one of plane portions 2-1 and 2-2 (plane portion 2-1 in the example shown in FIG. 7), an incidence window 5 for directing light emitted through incidence side fiber 20 into the integrating space formed by quarter-spherical portion 1# and plane portions 2-1 and 2-2, and an emission window 6 for attaching emission side fiber 30 thereto are formed. It is noted that incidence window 5 and emission window 6 may be disposed at any of plane portions 2-1 and 2-2 as long as incidence window 5 and emission window 6 are formed on a common plane.

The optical measurement apparatus according to the second modification of the present embodiment is similar to that shown in FIG. 4 except that fiber coupler 10B is used, and the detailed description thereof will not be repeated. Specifically, the number of fiber elements 22 constituting incidence side fiber 20 each for propagating light to be measured is not particularly limited. Further, in fiber coupler 10B according to the second modification of the present embodiment, incidence side fiber 20 and emission side fiber 30 may be integrated as shown in FIG. 6 to pass through plane portion 2-1 or 2-2.

Thus, the quarter-spherical integrator can be used to further downsize the apparatus.

<E. Applications>

Next, an example of applications using the above-described optical measurement apparatus will be described.

e1. Reflected Light Measurement System

Figure 8:
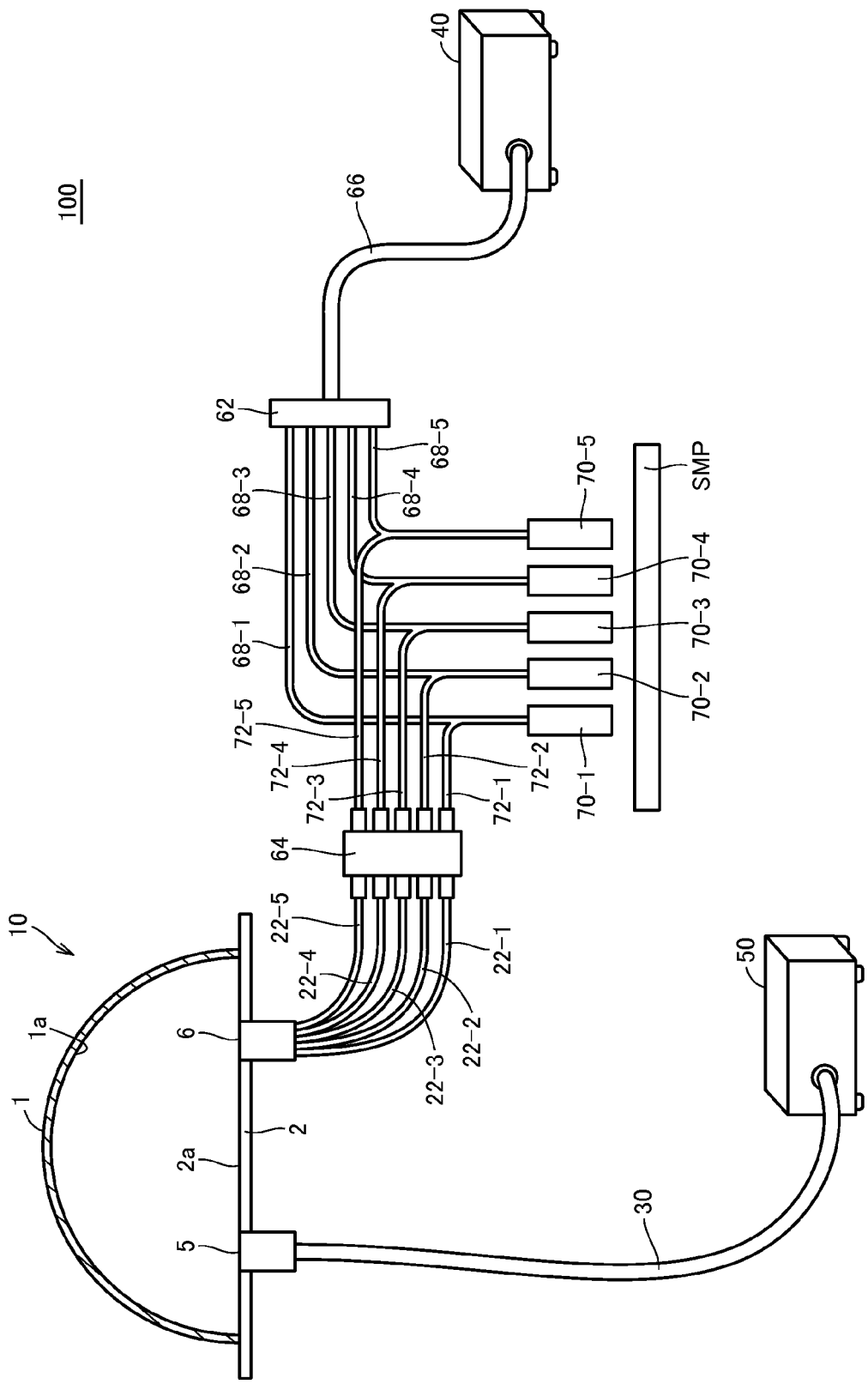
FIG. 8 schematically shows a reflected-light measurement system using the optical measurement apparatus according to the present embodiment.

FIG. 8 schematically shows a reflected light measurement system 100 using an optical measurement apparatus according to the present embodiment. Reflected light measurement system 100 shown in FIG. 8 measures reflected light generated at a surface of sample SMP to be measured to thereby evaluate reflection characteristics and surface characteristics of sample SMP to be measured.

Reflected light measurement system 100 includes, in addition to the optical measurement apparatus, a light source apparatus 40, an optical splitter 62, and a fiber switch unit 64.

Light source apparatus 40 generates reference light of a wavelength band appropriate for reflected light to be generated at sample SMP to be measured. The reference light generated from light source apparatus 40 is directed through a connection fiber 66 to optical splitter 62. Optical splitter 62 divides the reference light from light source apparatus 40 into multiple components. In the example shown in FIG. 8, optical splitter 62 divides the reference light from light source apparatus 40 into five components.

To the other end of optical splitter 62, five Y-shaped branch fibers are connected. The components of the divided reference light are output respectively to input fibers 68-1, 68-2, 68-3, 68-4, 68-5 of corresponding Y-shaped branch fibers. To respective leading ends of input fibers 68-1, 68-2, 68-3, 68-4, 68-5, emission/incidence portions 70-1, 70-2, 70-3, 70-4, 70-5 are connected respectively. The components of the reference light divided by optical splitter 62 are applied from emission/incidence portions 70-1, 70-2, 70-3, 70-4, 70-5 toward sample SMP to be measured.

The reference light is applied to sample SMP to be measured and, depending on the surface condition of sample SMP to be measured, components of the reference light are reflected to generate reflected light components. The generated reflected light components enter again emission/incidence portions 70-1, 70-2, 70-3, 70-4, 70-5, respectively.

The reflected light components entering emission/incidence portions 70-1, 70-2, 70-3, 70-4, 70-5 respectively are directed through corresponding output fibers 72-1, 72-2, 72-3, 72-4, 72-5 to fiber switch unit 64.

Fiber switch unit 64 has one end to which output fibers 72-1, 72-2, 72-3, 72-4, 72-5 are connected, and the other end to which fiber elements 22-1, 22-2, 22-3, 22-4, 22-5 constituting incidence side fiber 20 are connected. Fiber switch unit 64 responds to a switch instruction (not shown) to optically connect a specified output fiber 72 and its corresponding fiber element 22. For example, in response to a switch instruction for activating a first passage that is given to fiber switch unit 64, fiber switch unit 64 directs the reflected light propagating through output fiber 72-1 to the corresponding fiber element 22-1. Fiber switch unit 64 operates in this way to direct the reflected light propagating in a specified output fiber 72 to fiber coupler 10.

The operation of fiber coupler 10 has been described above, and the detailed description thereof will not be repeated.

Reflected light measurement system 100 shown in FIG. 8 is adapted to a situation where the surface condition of a film or the like manufactured to extend in the longitudinal direction is evaluated at multiple points along the direction of the shorter side.

e2. Transmitted Light Measurement System

Figure 9:
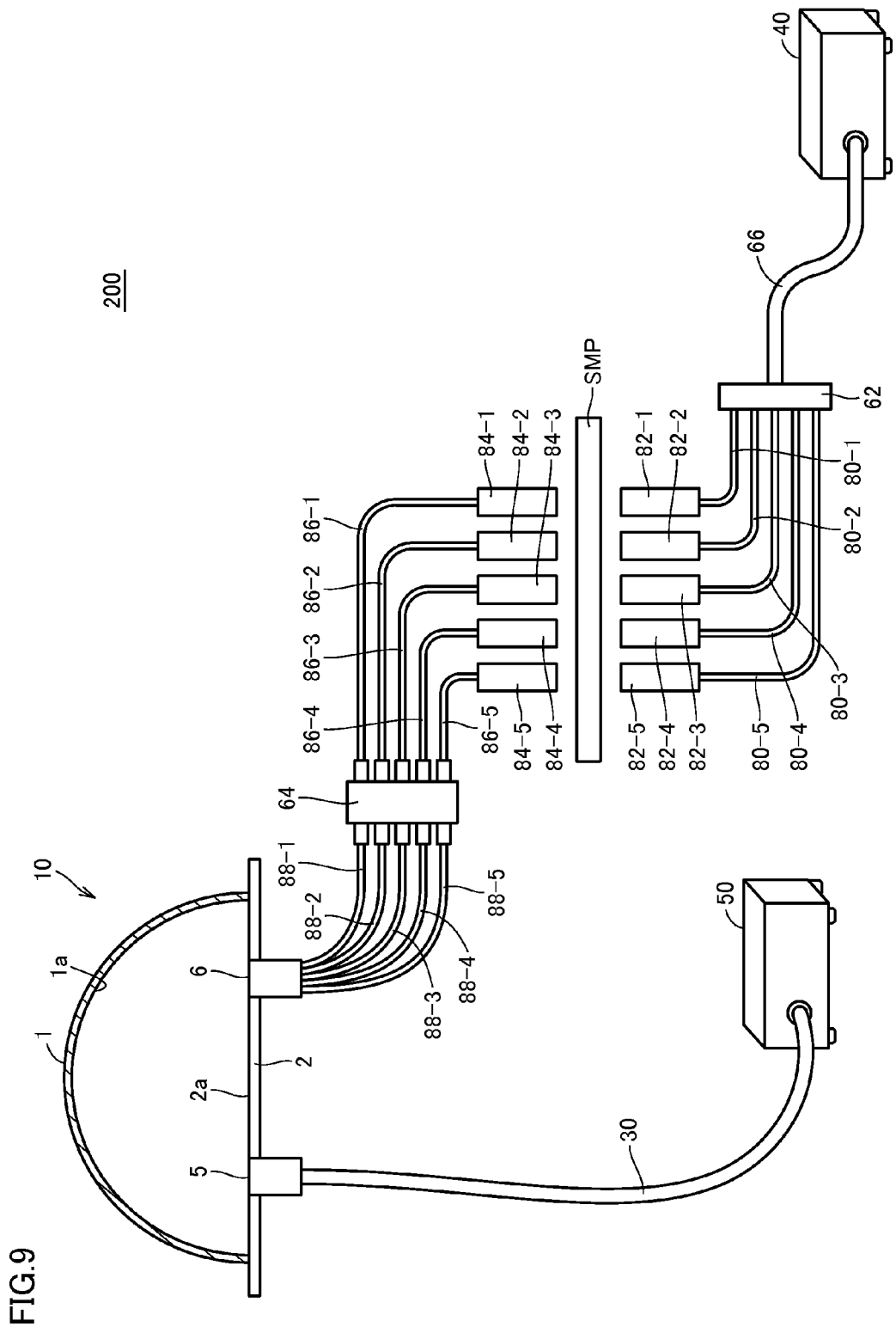
FIG. 9 schematically shows a transmitted-light measurement system using the optical measurement apparatus according to the present embodiment.

FIG. 9 schematically shows a transmitted light measurement system using an optical measurement apparatus according to the present embodiment. Transmitted light measurement system 200 shown in FIG. 9 measures transmitted light generated at sample SMP to be measured to evaluate transmission characteristics, thickness, and the like of sample SMP to be measured. Basically, transmitted light measurement system 200 is configured in such a manner that, in reflected light measurement system 100 shown in FIG. 8, reference light from light source apparatus 40 is applied to one side of sample SMP to be measured, and the transmitted light is received on the other side of sample SMP to be measured.

To optical splitter 62, input fibers 80-1, 80-2, 80-3, 80-4, 80-5 are connected for directing the reference light to emission portions 82-1, 82-2, 82-3, 82-4, 82-5 respectively that are aligned on one side of sample SMP to be measured. To fiber switch unit 64, output fibers 86-1, 86-2, 86-3, 86-4, 86-5 are connected for directing the transmitted light received at incidence portions 84-1, 84-2, 84-3, 84-4, 84-5 that are aligned on the other side of sample SMP to be measured.

The operation of fiber coupler 10 has been described above, and the detailed description thereof will not be repeated.

Transmitted light measurement system 200 shown in FIG. 9 is adapted to a situation where the thickness of a film or the like manufactured to extend in the longitudinal direction is evaluated at multiple points along the direction of the shorter side.

e3. Light Source Evaluation System

Figure 10:
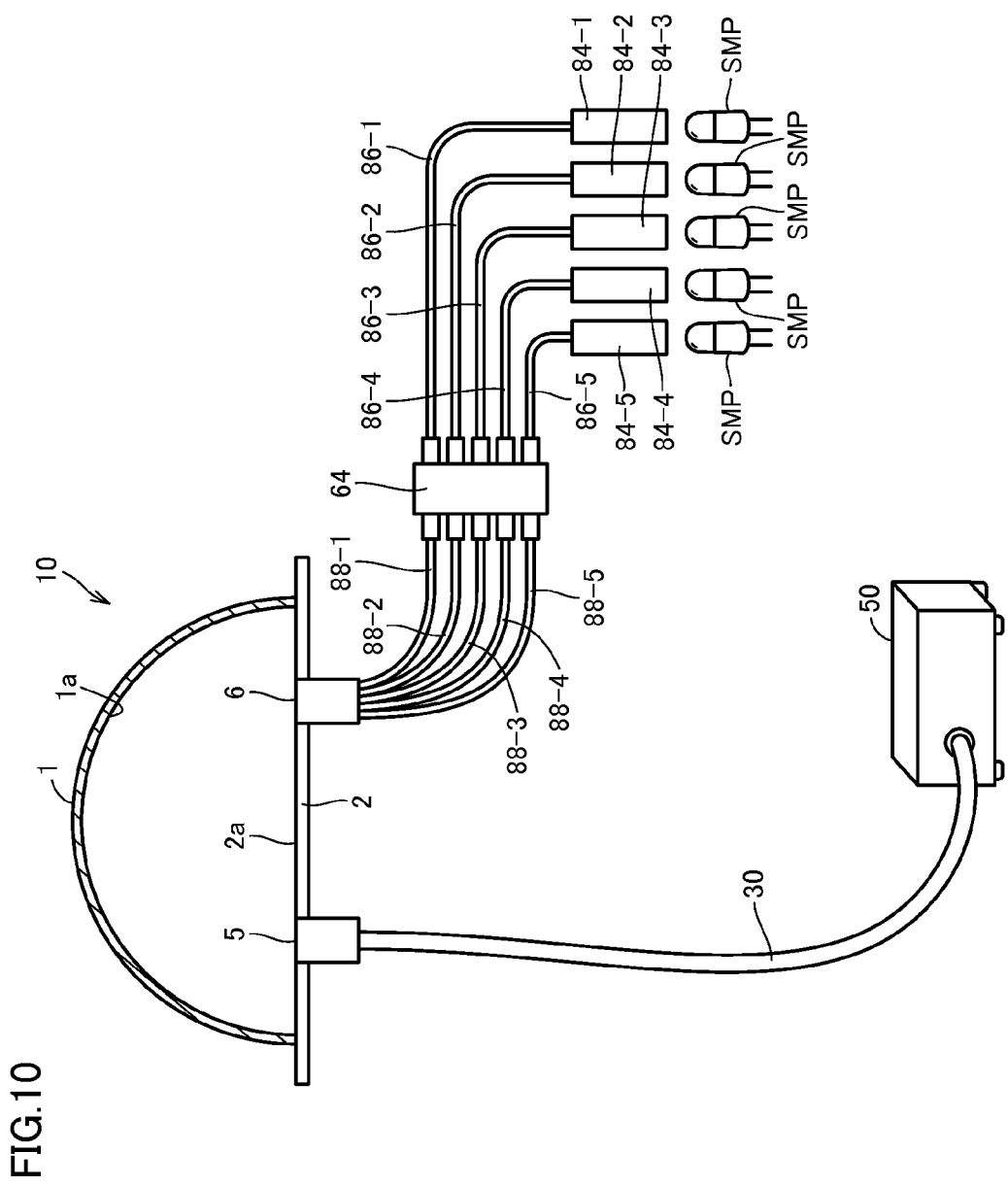
FIG. 10 schematically shows a light source evaluation system using the optical measurement apparatus according to the present embodiment.

FIG. 10 schematically shows a light source evaluation system using an optical measurement apparatus according to the present embodiment. Light source evaluation system 300 shown in FIG. 10 evaluates a light source (light emitting body) such as LED (Light Emitting Diode) as sample SMP to be measured. Basically, light source evaluation system 300 corresponds to a configuration in which instead of sample SMP to be measured and the structure for applying the reference light to sample SMP to be measured in transmitted light measurement system 200 shown in FIG. 9, incidence portions 84-1, 84-2, 84-3, 84-4, 84-5 are arranged in association with a plurality of LEDs that are samples SMP to be measured.

This light source evaluation system 300 evaluates the performance such as chromaticity, illuminance, brightness, color rendering index, and main wavelength of emitted light, of a plurality of LEDs that are samples SMP to be measured.

<F. Conclusion>

The optical measurement apparatus according to the present embodiment includes, on the input side of the spectroscopic measurement device, a fiber coupler formed of a hemispherical integrator or a quarter-spherical integrator, and therefore, measurement errors due to variation in the distribution of light emitted from an optical fiber can be reduced.

Further, the optical measurement apparatus according to the present embodiment uses a hemispherical integrator or a quarter-spherical integrator as the fiber coupler, and therefore, the apparatus configuration can further be downsized. At the same time, no baffle (light blocking plate) in the integrator is necessary, and therefore no self-absorption of the baffle occurs. Accordingly, the transmission efficiency of the light to be measured (measurement efficiency) can be enhanced to improve the measurement sensitivity.

Moreover, the optical measurement apparatus according to the present embodiment can reduce, in addition to the influence of variation in the distribution of light, measurement errors due to polarization characteristics.

Although the present invention has been described and illustrated in detail, it is clearly understood that the same is by way of illustration and example only and is not to be taken by way of limitation, the scope of the present invention being interpreted by the terms of the appended claims.

What is claimed is:

1. An optical measurement apparatus comprising:
   a spectroscopic measurement device;
   a first optical fiber for propagating light to be measured;
   a hemispherical portion having a light diffuse reflection layer on an inner wall of the hemispherical portion;
   a plane portion disposed to close an opening of said hemispherical portion and having a mirror reflection layer located to face the inner wall of said hemispherical portion, said plane portion including a first window for directing the light emitted through said first optical fiber into an integrating space, said integrating space being formed by said hemispherical portion and said plane portion; and
   a second optical fiber for propagating the light in said integrating space to said spectroscopic measurement device through a second window in said plane portion.

2. The optical measurement apparatus according to claim 1, wherein
   said first optical fiber includes a plurality of optical fiber elements each propagating the light to be measured.

3. The optical measurement apparatus according to claim 1, wherein
   at said plane portion, said first window and said second window are arranged apart from each other by a predetermined distance.

4. The optical measurement apparatus according to claim 1, wherein
   said first optical fiber and said second optical fiber are integrated to pass through said plane portion.

5. An optical measurement apparatus comprising:
   a spectroscopic measurement device;
   a first optical fiber for propagating light to be measured;
   a quarter-spherical portion having a light diffuse reflection layer on an inner wall of the quarter-spherical portion;
   a first plane portion and a second plane portion disposed to close an opening of said quarter-spherical portion and each having a mirror reflection layer located to face the inner wall of said quarter-spherical portion, one of said first plane portion and said second plane portion including a first window for directing the light emitted through said first optical fiber into an integrating space, said integrating space being formed by said quarter-spherical portion, said first plane portion, and said second plane portion; and
   a second optical fiber for propagating the light in said integrating space to said spectroscopic measurement device through a second window in said one of said first plane portion and said second plane portion to which said first optical fiber is connected.

6. The optical measurement apparatus according to claim 5, wherein
   said first optical fiber includes a plurality of optical fiber elements each propagating the light to be measured.

7. The optical measurement apparatus according to claim 5, wherein
   at the plane portion to which said first optical fiber is connected, said first window and said second window are arranged apart from each other by a predetermined distance.

8. The optical measurement apparatus according to claim 5, wherein
   said first optical fiber and said second optical fiber are integrated to pass through the plane portion to which said first optical fiber is connected.

9. An optical measurement system comprising:
   a light source;
   a spectroscopic measurement device;
   a light splitter for dividing light from said light source into a plurality of light source components;
   a first optical fiber for propagating a plurality of light components depending on a characteristic of an object to be measured that are obtained by applying the plurality of light source components from said light splitter to the object to be measured;
   a hemispherical portion having a light diffuse reflection layer on an inner wall of the hemispherical portion;
   a plane portion disposed to close an opening of said hemispherical portion and having a mirror reflection layer located to face the inner wall of said hemispherical portion; said plane portion including a first window for directing light emitted through said first optical fiber into an integrating space, said integrating space being formed by said hemispherical portion and said plane portion; and
   a second optical fiber for propagating the light in said integrating space to said spectroscopic measurement device through a second window in said plane portion.

10. A fiber coupler connected to an input side of a spectroscopic measurement device, said fiber coupler comprising:

a hemispherical portion having a light diffuse reflection layer on an inner wall of the hemispherical portion; and a plane portion disposed to close an opening of said hemispherical portion and having a mirror reflection layer located to face the inner wall of said hemispherical portion, said plane portion including:

a first window connected to a first optical fiber for propagating light to be measured and directing light emitted through said first optical fiber into an integrating space, said integrating space being formed by said hemispherical portion and said plane portion; and a second window connected to a second optical fiber for propagating the light in said integrating space to said spectroscopic measurement device.

11. The optical measurement apparatus according to claim 1, wherein said plane portion contains a first opening within which said first window is provided and a second opening within which said second window is provided, and said plane portion does not contain any additional openings that allow light to propagate through the plane portion.

12. The optical measurement apparatus according to claim 11, wherein said hemispherical portion has a center of curvature, said center of curvature being provided at a location on said plane portion, and said first window and said second window not being provided the location on said plane portion at which said center of curvature is located.

13. The optical measurement apparatus according to claim 11, wherein said hemispherical portion has a center of curvature, said center of curvature being provided at a location on said plane portion, and said first window and said second window being offset from the location on said plane portion at which said center of curvature is located by a predetermined distance.

14. The optical measurement system according to claim 9, wherein said plane portion contains a first opening within which said first window is provided and a second opening within which said second window is provided, and said plane portion does not contain any additional openings that allow light to propagate through the plane portion.

15. The optical measurement system according to claim 14, wherein said hemispherical portion has a center of curvature, said center of curvature being provided at a location on said plane portion, and said first window and said second window not being provided the location on said plane portion at which said center of curvature is located.

16. The optical measurement system according to claim 14, wherein said hemispherical portion has a center of curvature, said center of curvature being provided at a location on said plane portion, and said first window and said second window being offset from the location on said plane portion at which said center of curvature is located by a predetermined distance.

17. The fiber coupler according to claim 10, wherein said plane portion contains a first opening within which said first window is provided and a second opening within which said second window is provided, and said plane portion does not contain any additional openings that allow light to propagate through the plane portion.

18. The fiber coupler according to claim 17, wherein said hemispherical portion has a center of curvature, said center of curvature being provided at a location on said plane portion, and said first window and said second window not being provided the location on said plane portion at which said center of curvature is located.

19. The fiber coupler according to claim 17, wherein said hemispherical portion has a center of curvature, said center of curvature being provided at a location on said plane portion, and said first window and said second window being offset from the location on said plane portion at which said center of curvature is located by a predetermined distance.

* * * * *